United States Patent
Zhang et al.

(10) Patent No.: US 11,618,732 B2
(45) Date of Patent: Apr. 4, 2023

(54) PROCESS FOR THE SYNTHESIS OF N-SUBSTITUTED LACTAMS AND AMIDES

(71) Applicant: AdvanSix Resins & Chemicals LLC, Parsippany, NJ (US)

(72) Inventors: Xiawei Zhang, West Chester, PA (US); Robert Schutter, Jr., Sewell, NJ (US); Lihao Tang, Bridgewater, NJ (US); Scott Keenan, Marlton, NJ (US); Xin Li, Broomall, PA (US)

(73) Assignee: AdvanSix Resins & Chemical LLC, Parsippany, NJ (US)

( * ) Notice: Subject to any disclaimer, the term of this patent is extended or adjusted under 35 U.S.C. 154(b) by 213 days.

(21) Appl. No.: 17/115,396

(22) Filed: Dec. 8, 2020

(65) Prior Publication Data
US 2021/0179562 A1 Jun. 17, 2021

Related U.S. Application Data

(60) Provisional application No. 62/946,591, filed on Dec. 11, 2019.

(51) Int. Cl.
| | | |
|---|---|---|
| *C07D 201/02* | (2006.01) | |
| *C07D 207/12* | (2006.01) | |
| *C07D 223/10* | (2006.01) | |
| *C07D 223/04* | (2006.01) | |
| *B01J 23/44* | (2006.01) | |

(52) U.S. Cl.
CPC ............ *C07D 223/04* (2013.01); *B01J 23/44* (2013.01)

(58) Field of Classification Search
CPC ... C07D 201/02; C07D 207/12; C07D 223/10
See application file for complete search history.

(56) References Cited

U.S. PATENT DOCUMENTS 3,073,843 A   1/1963   Buc

FOREIGN PATENT DOCUMENTS

| CN | 101415673 A | 4/2009 |
|---|---|---|
| EP | 0037603 A1 | 10/1981 |
| TW | 201942310 A | 11/2019 |
| WO | 2007/115943 A2 | 10/2007 |
| WO | 2019/190997 A1 | 10/2019 |

OTHER PUBLICATIONS

International Search Report and Written Opinion received for PCT Patent Application No. PCT/US20/63790, dated Mar. 4, 2021, 10 pages.
Recueil des Travaux Chimiques des Pays-Bas, "Reductive O- and N-alkylations. Alternative catalytic methods to nucleophilic substitution", 1996, 115, 231-238.

*Primary Examiner* — Bruck Kifle
(74) *Attorney, Agent, or Firm* — Faegre Drinker Biddle & Reath LLP

(57) ABSTRACT

A process for the synthesis of N-alkylated lactams via reductive alkylation. The process of the present disclosure may be conducted by the addition of an aldehyde to a lactam in the presence of a catalyst under a reducing atmosphere.

8 Claims, No Drawings

PROCESS FOR THE SYNTHESIS OF N-SUBSTITUTED LACTAMS AND AMIDES

CROSS-REFERENCE TO RELATED APPLICATION

This application claims priority to U.S. Provisional Application No. 62/946,591, filed Dec. 11, 2019, the disclosure of which is herein incorporated by reference in its entirety.

BACKGROUND

1. Field of the Disclosure

The present disclosure relates to a process for synthesizing N-substituted lactams and amides via reductive N-alkylation.

2. Description of the Related Art

N-substituted amides, particularly N-alkylated lactams, are desirable molecules for use in a wide range of applications. Reactions to prepare N-substituted amides and lactams are widely used in synthesis of drugs by pharmaceutical industry, synthesis of fertilizers, pesticides, and other products, as well as in the synthesis of chemical intermediates.

One such reaction is the synthesis of N-alkyl caprolactams. N-alkyl caprolactams are usually synthesized via alkylation, using either sodium metal or sodium hydride as the deprotonating agent and an alkyl halide as the alkylating agent. These reagents may be hazardous and difficult to handle and may generate significant amounts of solid waste, and difficulties in handling and waste disposal may add to the cost of synthesis.

Furthermore, a process solvent (usually ethyl acetate) is required for known alkylation reactions. Significant amounts of dehydrating agents such as anhydrous sodium sulfate ($Na_2SO_4$) and high-pressure hydrogen gas ($H_2$) (over 550 psi) are also needed. These reaction conditions make the large-scale syntheses of N-alkylcaprolactams and other N-alkylamides impractical for industrial use.

What is needed is to a process for synthesizing N-substituted lactams which is an improvement over the foregoing.

SUMMARY

The present disclosure provides a process for the synthesis of N-alkylated lactams via reductive alkylation. The process of the present disclosure may be conducted by the addition of an aldehyde to a lactam in the presence of a catalyst under a reducing atmosphere.

The present disclosure provides a process for preparing a substituted lactam, comprising reacting a lactam of the following formula:

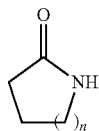

wherein n is 0, 1, 2, or 3, with an alkylating agent selected from paraformaldehyde and an aldehyde of the following formula:

wherein R is H or $C_1$-$C_6$ alkyl; in the presence of a catalyst; hydrogen; and a total content of process solvents of less than 1500 ppm, to form water and an N-substituted lactam of the following formula:

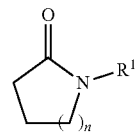

wherein n is 0, 1, 2, or 3, and $R^1$ is $C_1$-$C_6$ alkyl.

The present disclosure further provides a process for preparing a substituted lactam, comprising: reacting caprolactam with an alkylating agent selected from paraformaldehyde, formaldehyde, and acetaldehyde; in the presence of a catalyst; hydrogen; and a total content of process solvents of less than 1500 ppm, to form water and an N-substituted lactam selected from the group consisting of N-methylcaprolactam and N-ethylcaprolactam.

The present disclosure also provides an N-substituted lactam selected from the group consisting of N-methylcaprolactam and N-ethylcaprolactam, in liquid form, having a total process solvent content of less than 1500 ppm, based on the total weight of the lactam.

The above mentioned and other features of the disclosure, and the manner of attaining them, will become more apparent and will be better understood by reference to the following description of embodiments taken in conjunction with the accompanying drawings.

DETAILED DESCRIPTION

N-alkyl caprolactams are a group of compounds that have many potential uses in paints and coatings, agricultural industries, and electronics, among others. Alkylated amides, including alkylated caprolactams, can be synthesized via reductive N-alkylation using palladium on carbon catalysts and carbonyl compounds as the alkylating agents. However, the use of small aldehydes, such as acetaldehyde and formaldehyde, as the alkylating agents, has not been previously reported.

Unlike known synthetic methods, which rely on the use of sodium metal or sodium hydride (NaH) as deprotonating agents in conjunction with alkyl halides, the process of the present disclosure may be used to synthesize N-alkylated amides in high yield via reductive N-alkylation of amides, such as caprolactam. These reactions use cheap and safe starting material, such as caprolactam and acetaldehyde, for example. The process of the current disclosure is easy to perform and generates very little waste, with water as the major by-product and small amounts of ethanol and acetal as minor by-products. Furthermore, the process of the present disclosure may be conducted without any process solvents or dehydrating agent, thereby eliminating the need to remove process solvent or separate the dehydrating agent.

The present disclosure provides a process by which N-ethylcaprolactam (NEC), N-methylcaprolactam (NMC), and other N-alkylamides may be prepared from caprolactam or other amides through reductive N-alkylation, as shown below in Scheme 1:

SCHEME 1

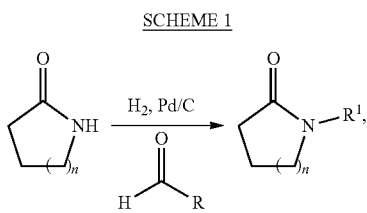

wherein n is 0, 1, 2, or 3;
R is H or $C_1$-$C_6$ alkyl; and
$R^1$ is $C_1$-$C_6$ alkyl.

Thus, the reactant lactams may include β-propiolactam, γ-butyrolactam, δ-valerolactam, and ε-caprolactam.

It has surprisingly been found that these reactions may be carried out without the use of any dehydrating agent, thereby eliminating the need to separate the dehydrating agent from the product. The process of the current disclosure may also be conducted without relying on high pressures, thus reducing the need for reaction vessels capable of withstanding high pressures. Advantageously, it has further been found that these reactions may be carried out under conditions free of process solvent, as described below, thus significantly limiting the amount of waste generated.

The reaction may be conducted by combining the amide with an excess of the aldehyde under a hydrogen atmosphere in the presence of a catalyst.

The molar ratio of amide to aldehyde may be 1.0:1.5 or greater, 1.0 to 2.0 or greater, 1.0:3.0 or greater, 1.0:4.0 or greater, 1.0:5.0 or greater, or 1.0:6.0 or less, 1.0:7.0 or less, 1.0:8.0 or less, 1.0:9.0 or less, 1.0:10.0 or less, or within any range defined between and including any two of the foregoing values.

The catalyst may be selected from palladium, platinum, nickel, rhodium, and iridium. The catalyst may include a support, such as activated carbon.

The amount of catalyst present as a mole percentage of the amide may be 0.1% or greater, 0.2% or greater, 0.4% or greater, 0.6% or greater, or 1.0% or less, 2.0% or less, 3.0% or less, 4.0% or less, 5.0% or less, or within any range defined between and including any two of the foregoing values.

The pressure of the hydrogen gas may be 100 psi or lower, 120 psi or lower, 150 psi or lower, 160 psi or lower, 170 psi or lower, 190 psi or lower, 200 psi or lower, 250 psi or lower, or within any range defined between and including any two of the foregoing values.

The reaction may be conducted at a temperature of 40° C. or greater, 50° C. or greater, 60° C. or greater, 80° C. or greater, 100° C. or greater, or 110° C. or lower, 120° C. or lower, 130° C. or lower, 150° C. or lower, 170° C. or lower, 200° C. or lower, or within any range defined between and including any two of the foregoing values.

The reaction time may be 2 hours or longer, 4 hours or longer, 6 hours or longer, 10 hours or longer, 12 hours or longer, 15 hours or longer, or 16 hours or less, 18 hours or less, 20 hours or less, 22 hours or less, 24 hours or less, 30 hours or less, or within any range defined between and including any two of the foregoing values.

"Process solvent", as used herein, will be understood to include water, aqueous mixtures, and organic liquids. It will be understood that process solvents do not include the reactants or products of the reaction. "Process solvent-free" or "process solvent-free conditions", as used herein, will be understood to indicate that the amount of process solvent present in the reaction is 1500 ppm or less, 1000 ppm or less, 800 ppm or less, 500 ppm or less, 100 ppm or less, 50 ppm or less, or within any range defined between and including any two of the foregoing values.

As an example, this process may be used in the synthesis of N-ethylcaprolactam (NEC), as shown below in Scheme 2. As shown in Scheme 2, the reaction may be carried out under process solvent-free conditions, without the need for a dehydrating agent.

SCHEME 2

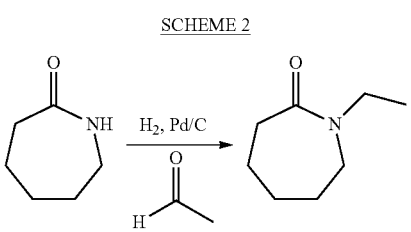

Alternatively, the alkylating agent may be paraformaldehyde. As shown in Scheme 3, the use of paraformaldehyde permits the synthesis of N-methylcaprolactam (NMC). Again, the reaction may be carried out under process solvent-free conditions, without the need for a dehydrating agent.

SCHEME 3

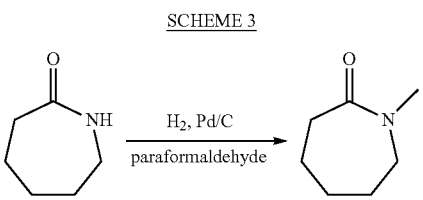

In comparison to known processes, the process of the present disclosure reduces both costs and waste by eliminating the need for process solvent and/or dehydrating agents. Furthermore, the process of the present disclosure uses a lower pressure hydrogen atmosphere, thereby saving costs due to less stringent requirements for reaction vessels.

The process of the present disclosure allows for high-yielding, streamlined synthesis of N-alkylcaprolactams using safe starting materials and producing small amounts of waste.

As used herein, the phrase "within any range defined between and including any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

The following non-limiting Examples serve to illustrate the disclosure.

EXAMPLES

Example 1: Preparation of N-ethyl Caprolactam

One equivalent of caprolactam, 0.5 mole % palladium on carbon catalyst, and 4 equivalents acetaldehyde were combined in a reaction vessel under hydrogen atmosphere (150 psi). The mixture was heated to 100° C. for 21 hours. N-ethyl caprolactam (NEC) was obtained in 99.6% yield, as determined by GC analysis. After filtration, the filtrate was distilled to obtain N-ethyl caprolactam at greater than 99.5 wt. % purity with less than 0.1 wt. % caprolactam remaining.

Example 2: Preparation of N-methyl Caprolactam

Caprolactam (40.0 g, 0.353 mol) was added to a reaction vessel, followed by paraformaldehyde (42.5 g, 1.41 mol). A 10% palladium on carbon catalyst (4.05 g, 0.004 mol) was added. The reaction vessel was sealed, then purged and charged with H$_2$ (150 psi). The mixture was heated to 100° C. and stirred for 18 hours. GC analysis showed that N-methyl caprolactam was formed in 71% yield. After filtration, the filtrate was distilled to obtain the pure N-methyl caprolactam product.

ASPECTS

Aspect 1 is a process for preparing a substituted lactam, comprising: reacting a lactam of the following formula:

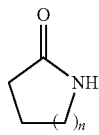

wherein n is 0, 1, 2, or 3,
with an alkylating agent selected from paraformaldehyde and an aldehyde of the following formula:

wherein R is H or C$_1$-C$_6$ alkyl; in the presence of a catalyst; hydrogen; and a total content of process solvents of less than 1500 ppm, to form water and an N-substituted lactam of the following formula:

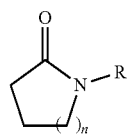

wherein n is 0, 1, 2, or 3, and R$^1$ is C$_1$-C$_6$ alkyl.

Aspect 2 is the process of Aspect 1, wherein the total content of process solvents is less than 1000 ppm.

Aspect 3 is the process of either Aspect 1 or Aspect 2, wherein the catalyst is a palladium catalyst.

Aspect 4 is the process of any of Aspects 1-3, wherein the reacting step is carried out at a temperature from 50° C. to 200° C.

Aspect 5 is the process of any of Aspects 1-4, wherein the reacting step is carried out in the presence of a hydrogen atmosphere at a pressure of 100 psi to 200 psi.

Aspect 6 is the process of any of Aspects 1-5, wherein the lactam is caprolactam and the N-substituted lactam is N-methylcaprolactam.

Aspect 7 is the process of any of Aspects 1-5, wherein the lactam is caprolactam and the N-substituted lactam is N-ethylcaprolactam.

Aspect 8 is the process of any of Aspects 1-7, wherein the N-substituted lactam is obtained at a yield of greater than 90%.

Aspect 9 is a process for preparing a substituted lactam, comprising: reacting caprolactam with an alkylating agent selected from paraformaldehyde, formaldehyde, and acetaldehyde; in the presence of a catalyst; hydrogen; and a total content of process solvents of less than 1500 ppm, to form water and an N-substituted lactam selected from the group consisting of N-methylcaprolactam and N-ethylcaprolactam.

Aspect 10 is the process of Aspect 9, wherein the total content of process solvents is less than 1000 ppm.

Aspect 11 is the process of either of Aspect 9 or Aspect 10, wherein the catalyst is a palladium catalyst.

Aspect 12 is the process of any of Aspects 9-11, wherein the reacting step is carried out at a temperature from 50° C. to 200° C.

Aspect 13 is the process of any of Aspects 9-12, wherein the reacting step is carried out in the presence of a hydrogen atmosphere at a pressure of 100 to 200 psi.

Aspect 14 is the process of any of Aspects 9-13, wherein the N-substituted lactam is N-methylcaprolactam.

Aspect 15 is the process of any of Aspects 9-13, wherein the N-substituted lactam is N-ethylcaprolactam.

Aspect 16 is the process of any of Aspects 9-15, wherein the N-substituted lactam is obtained at a yield of greater than 90%.

Aspect 17 is an N-substituted lactam selected from the group consisting of N-methylcaprolactam and N-ethylcaprolactam, in liquid form, having a total process solvent content of less than 1500 ppm, based on the total weight of the lactam.

Aspect 18 is the lactam of Aspect 17, wherein the total process solvent content is less than 1000 ppm.

Aspect 19 is the lactam of either of Aspect 17 or Aspect 18, wherein the N-substituted lactam is N-methylcaprolactam.

Aspect 20 is the lactam of either of Aspects 17 or Aspect 18, wherein the N-substituted lactam is N-ethylcaprolactam.

While this disclosure has been described as relative to exemplary designs, the present disclosure may be further modified within the spirit and scope of this disclosure. Further, this application is intended to cover such departures from the present disclosure as come within known or customary practice in the art to which this disclosure pertains.

What is claimed is:

1. A process for preparing a substituted lactam, comprising:
    reacting caprolactam with an alkylating agent selected from paraformaldehyde, formaldehyde, and acetaldehyde;
    in the presence of:
        a catalyst;
        hydrogen; and
        optionally, process solvents, a total content of the process solvents of less than 1500 ppm,
    to form water and an N-substituted lactam selected from the group consisting of N-methylcaprolactam and N-ethylcaprolactam.

2. The process of claim 1, wherein the total content of process solvents is less than 1000 ppm.

3. The process of claim 1, wherein the catalyst is a palladium catalyst.

4. The process of claim 1, wherein the reacting step is carried out at a temperature from 50° C. to 200° C.

5. The process of claim 1, wherein the reacting step is carried out in the presence of a hydrogen atmosphere at a pressure of 100 to 200 psi.

6. The process of claim 1, wherein the N-substituted lactam is N-methylcaprolactam.

7. The process of claim 1, wherein the N-substituted lactam is N-ethylcaprolactam.

8. The process of claim 1, wherein the N-substituted lactam is obtained at a yield of greater than 90%.

* * * * *